United States Patent
Sugiyama et al.

(10) Patent No.: US 9,056,209 B2
(45) Date of Patent: Jun. 16, 2015

(54) APIGENIN-CONTAINING COMPOSITION

(75) Inventors: Mitsuru Sugiyama, Haga-gun (JP); Shinya Kasamatsu, Haga-gun (JP)

(73) Assignee: Kao Corporation, Tokyo (JP)

( * ) Notice: Subject to any disclaimer, the term of this patent is extended or adjusted under 35 U.S.C. 154(b) by 136 days.

(21) Appl. No.: 13/320,470

(22) PCT Filed: Jun. 2, 2010

(86) PCT No.: PCT/JP2010/003680
§ 371 (c)(1),
(2), (4) Date: Nov. 14, 2011

(87) PCT Pub. No.: WO2010/146788
PCT Pub. Date: Dec. 23, 2010

(65) Prior Publication Data
US 2012/0100088 A1    Apr. 26, 2012

(30) Foreign Application Priority Data

Jun. 17, 2009 (JP) .................................. 2009-144398
Jun. 17, 2009 (JP) .................................. 2009-144399

(51) Int. Cl.
*A61K 8/34*    (2006.01)
*A61K 8/49*    (2006.01)
*A61K 31/353*    (2006.01)
*A61Q 19/02*    (2006.01)
*A61K 9/00*    (2006.01)
*A61K 47/10*    (2006.01)
*A61K 9/08*    (2006.01)
*A61K 31/055*    (2006.01)

(52) U.S. Cl.
CPC ............... *A61Q 19/02* (2013.01); *A61K 8/347* (2013.01); *A61K 8/498* (2013.01); *A61K 9/0014* (2013.01); *A61K 47/10* (2013.01); *A61K 9/08* (2013.01); *A61K 31/055* (2013.01); *A61K 31/353* (2013.01)

(58) Field of Classification Search
None
See application file for complete search history.

(56) References Cited

U.S. PATENT DOCUMENTS 6,281,236 B1 *    8/2001    Farber .......................... 514/390

FOREIGN PATENT DOCUMENTS

| CN | 1441672 A | 9/2003 | |
| JP | 07-330569 A | 12/1995 | |
| JP | A-9-263534 | 10/1997 | |
| JP | 10203921 A * | 8/1998 | ............... A61K 7/00 |
| JP | A-10-203921 | 8/1998 | |
| JP | A-2003-505404 | 2/2003 | |
| JP | A-2004-002264 | 1/2004 | |
| JP | A-2004-091338 | 3/2004 | |
| JP | 2005-187986 A | 7/2005 | |
| JP | A-2005-289880 | 10/2005 | |
| JP | 2006-327967 A | 12/2006 | |
| JP | A-2006-327988 | 12/2006 | |
| JP | A-2007-008847 | 1/2007 | |
| JP | 2007031301 A * | 2/2007 | ............... A61K 8/96 |
| JP | A-2007-031301 | 2/2007 | |
| WO | WO 01/87301 A1 | 11/2001 | |

OTHER PUBLICATIONS

JP2007-31301, Machine Translation, Published Feb. 2007.*
JP1998-203921, Machine Translation, Published Aug. 4, 1998.*
JP 2007-031301, Ono et al., Machine Translation, Published, Feb. 8, 2007.*
JP 10-203921, Tsukada et al., Machine Translation, Published, Aug. 4, 1998.*
International Search Report (ISR) for PCT/JP2010/003680, I.A. fd: Jun. 2, 2010, mailed Jun. 29, 2010 from the Japanese Patent Office, Tokyo, Japan.
International Preliminary Report on Patentability (Chapter I of the Patent Cooperation Treaty) including the Written Opinion for PCT/JP2010/003680, I.A. fd: Jun. 2, 2010, issued Jan. 17, 2012, from the International Bureau of WIPO, Genera, Switzerland.
Notification of First Office Action for Chinese Patent Application No. 201080021451.3, mailed Sep. 26, 2012, Patent Office of the People's Republic of China, Beijing, China.
"Chamomile ET" in New Cosmetics Handbook, Oct. 30, 2006, Nikko Chemicals Ltd. et al., p. 553.

* cited by examiner

*Primary Examiner* — Michael B Pallay
(74) *Attorney, Agent, or Firm* — Sterne, Kessler, Goldstein & Fox P.L.L.C.

(57) ABSTRACT

Provided is a composition which maintains apigenin stably. The present invention provides the composition containing apigenin at 3 ppm or more and dibutylhydroxytoluene, wherein the mass ratio of the content of apigenin relative to the content of dibutylhydroxytoluene is 1 or greater, or the pH value is less than 7. Also provided is a method for preparing an apigenin-containing composition, the method including combining 3 ppm or more of apigenin with dibutylhydroxytoluene so that the mass ratio of the content of apigenin relative to the content of dibutylhydroxytoluene is 1 or greater, or including adjusting the ph of the composition to a value less than 7.

26 Claims, No Drawings

APIGENIN-CONTAINING COMPOSITION

TECHNICAL FIELD OF THE INVENTION

The present invention relates to a composition which maintains apigenin stably.

BACKGROUND OF THE INVENTION

Apigenin is a flavonoid contained in plants such as wild chamomile (*Matricaria recutita* L.), Roman chamomile (*Anthemis nobilis* L.), dahlia (*Dahlia pinnata*), lilac daphne (*Daphne genkwa*) and sorghum (*Sorghum nervosum* Bess). As apigenin has a urease activity inhibitory action (Patent Document 1), an antioxidant action (Patent Document 2), a melanin production promoting action (Patent Document 3 and Patent Document 4), an anti-inflammatory action (Patent Document 5), a pigmentation inhibitory action (Patent Document 6) and the like, it is useful as a component for cosmetics, medicines, and quasi-drugs. Therefore, there have been hitherto reported various compositions containing apigenin or an apigenin-containing plant extract (Patent Documents 2 to 6).

Patent Document 1: JP-A-2004-91338
Patent Document 2: JP-A-2005-289880
Patent Document 3: JP-A-9-263534
Patent Document 4: JP-A-2004-2264
Patent Document 5: JP-A-2007-8847
Patent Document 6: JP-A-2006-327988

DISCLOSURE OF THE INVENTION

In one embodiment, the present invention provides a composition containing apigenin at 3 ppm or more and dibutylhydroxytoluene, wherein the mass ratio of the content of apigenin relative to the content of dibutylhydroxytoluene is 1 or greater, or the pH value of the composition is less than 7.

In another embodiment, the present invention provides a method for preparing an apigenin-containing composition, the method including combining 3 ppm or more of apigenin with dibutylhydroxytoluene, and adjusting the mass ratio of the content of apigenin relative to the content of dibutylhydroxytoluene to be 1 or greater, or adjusting the pH of the composition to a value less than 7.

In further another embodiment, the present invention provides a method for stabilizing apigenin in a composition containing apigenin and dibutylhydroxytoluene, the method including adjusting the mass ratio of the content of apigenin relative to the content of dibutylhydroxytoluene to be 1 or greater, or adjusting the pH of the composition to a value less than 7.

DETAILED DESCRIPTION OF THE INVENTION

The inventors of the present invention found, in the course of conducting an investigation on compositions containing apigenin at high concentrations, that when dibutylhydroxytoluene (BHT), which is a substance generally used as an antioxidant or the like, is coexisted in a composition containing apigenin, apigenin and BHT form an adduct, so that apigenin cannot be maintained stably in the composition.

Thus, the inventors of the present invention conducted an investigation to maintain apigenin stably in a composition in the presence of BHT. As a result, the inventors found that apigenin can be maintained stably in a composition by adjusting the mass ratio of the content of apigenin relative to the content of BHT in the composition to 1 or greater, or by adjusting the pH of the composition to a value less than 7.

According to the present invention, provided is a composition containing apigenin stably, and also provided is a medicine, a quasi-drug or a cosmetic material which can maximally exhibit the effects of apigenin as an active ingredient.

According to the present invention, apigenin means a compound represented by the following formula.

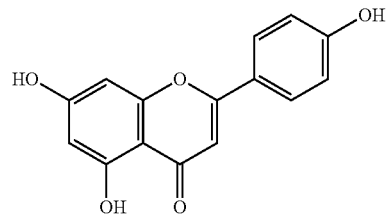 [SMILES: O=c1cc(-c2ccc(O)cc2)oc2cc(O)cc(O)c12]

Apigenin can be obtained according to a method conventionally known in the pertinent art. Typically, apigenin can be obtained from a plant containing apigenin, for example, a plant such as wild chamomile, Roman chamomile, dahlia, lilac daphne or sorghum, or an extract of the plants, and preferably from a high-concentration extract of the plants. Here, wild chamomile means *Matricaria recutita* L. of the family Asteraceae, and is also known as German chamomile. Furthermore, Roman chamomile means *Anthemis nobilis* L. of the family Asteraceae, and dahlia means *Dahlia pinnata* of the family Asteraceae. Lilac daphne means *Daphne genkwa* of the family Thymelaeaceae, and sorghum means *Sorghum nervosum* Bess of the family Gramineae.

Among the plants described above, plants of the Asteraceae are preferred, and from the viewpoint of obtaining a high-concentration apigenin-containing extract, wild chamomile and Roman chamomile are more preferred, while Roman chamomile is even more preferred.

For the plants containing apigenin, any parts of the plants listed above, for example, the whole plant, leaves, stems, sprouts, flowers, buds, woody part, bark, thalluses, roots, rhizomes, pseudobulbs, bulbs, tubers, seeds, fruits, sclerotia, resins, or combinations thereof can be used. In the case of wild chamomile and Roman chamomile, it is preferable to use the corolla of the flower or the buds. These parts are added to the composition of the present invention directly or after being crushed, cut or dried, or after being subjected to further processes such as extraction.

Examples of the extract of a plant containing apigenin include various solvent extracts obtainable by conventional methods, dilutions thereof, concentrates thereof, dried powders thereof, and extracts that have been treated with activated carbon. Among these, various solvent extracts are preferred. Alternately, commercially available extracts of the plants can also be used. A specific example of the method for extraction may be a method including immersing a plant in an extraction solvent in an amount of 5 to 40 times (mass ratio) the amount of the extraction raw material, performing extraction at normal temperature or under heating to reflux for one day to one month, and then filtering the extract to remove residues.

As the extraction solvent, any one of a polar solvent and a non-polar solvent can be used. Specific examples of the extraction solvent include, for example, water; alcohols such as methanol, ethanol, propanol, and butanol; polyhydric alcohols such as propylene glycol and butylene glycol; ketones such as acetone and methyl ethyl ketone; esters such as methyl acetate and ethyl acetate; linear and cyclic ethers such as tetrahydrofuran and diethyl ether; polyethers such as polyethylene glycol; hydrocarbons such as squalane, hexane, cyclohexane, and petroleum ether; aromatic hydrocarbons such as toluene; halogenated hydrocarbons such as dichloromethane, chloroform, and dichloroethane; and carbon dioxide. These can be used as mixtures. Among these, preferred specific examples include an aqueous ethanol solution, an aqueous butanediol solution, and an aqueous propylene glycol solution. An aqueous ethanol solution and an aqueous butanediol solution are more preferred, and an aqueous ethanol solution is even more preferred. The aqueous ethanol solution is preferably a 5 vol % to 99.5 vol % aqueous ethanol solution, and more preferably a 10 vol % to 80 vol % aqueous ethanol solution. When wild chamomile is used, a 5 vol % to 55 vol % aqueous ethanol solution is preferred, and a 10 vol % to 50 vol % aqueous ethanol solution is more preferred. When Roman chamomile is used, a 30 vol % to 99.5 vol % aqueous ethanol solution is preferred, and a 40 vol % to 80 vol % aqueous ethanol solution is more preferred. The amount of use of the solvent is about 10 to 40 times (mass ratio). The extraction time is preferably one day to one month, and the extraction temperature is preferably 5° C. to 80° C.

Even more preferably, an extract containing a higher concentration of apigenin can be obtained by further subjecting an extract obtained as described above to a three steps process described below, i.e., an adsorption step, a washing step and an elution step, according to the descriptions of Japanese Patent Application No. 2009-004378.

In the adsorption step, for example, the extract is contacted with or mixed in contact with an adsorptive carrier to obtain an adsorbate. Specific examples of the adsorptive carrier favorably include powdered cellulose, radiolite, and celite, and preferred examples include powdered cellulose, radiolite and a combination thereof. The adsorptive carrier is preferably used in an amount of about 2.5 g to 10 g per 200 mL of the extract, from the viewpoint of the recovery ratio of apigenin. Furthermore, in order to fortify the adsorption of apigenin to the adsorptive carrier, it is preferable to concentrate the extract of an apigenin-containing plant after contacting the extract with the carrier as described above. The concentration may be carried out according to a routine method, but specific examples of the technique for concentration include concentration under reduced pressure.

The washing step is carried out by, for example, contacting the adsorbate obtained in the previous step with water or a 20 vol % or less aqueous ethanol solution in an amount equivalent to 2 to 10 times the volume of the adsorbate. It is preferable to contact the adsorbate with water.

Specific examples of the technique for washing include filtration and decantation, and preferred examples include normal pressure filtration using a filter paper or a filter cloth; pressure filtration using a filter press, a pressure filtering machine using filter paper, a leaf filter, a rotary press or the like; and reduced pressure filtration using a rotating drum type continuous filtering machine, a vacuum filter or the like. In view of convenience, normal pressure filtration is preferred. When washing is carried out by filtration, apigenin is maintained in the adsorptive carrier, and other components are separated as a filtrate.

The elution step is carried out by contacting the washed adsorbate with a 40 vol % to 99.5 vol % aqueous ethanol solution in an amount equivalent to 2 to 10 times the volume of the adsorbate. Specific examples of the technique for elution include those used for washing as described above. When elution is carried out by filtration, apigenin is separated from the adsorptive carrier as a filtrate.

When the extract is subjected to the three steps process, obtained is a high-concentration apigenin-containing extract containing apigenin in an amount of 10% to 30% by mass, preferably 15% to 25% by mass, based on the evaporation residue.

The high-concentration apigenin-containing extract thus obtained may be further subjected to chromatography, liquid-liquid separation or the like, to remove inert impurities in the extract.

The high-concentration apigenin-containing extract can be used directly, but may also be used after the extract is diluted, concentrated or freeze-dried, or then prepared into a powder or a paste form.

Dibutylhydroxytoluene (BHT) is a well known substance that is used as an antioxidant or the like, and commercially available products thereof (for example, manufactured by Wako Pure Chemical Industries, Ltd., Code No. 047-29451) can be purchased.

The composition of the present invention can be prepared by combining apigenin with BHT, and adjusting the mass ratio of the content of apigenin relative to the content of BHT to be 1 or greater. The mass ratio is preferably 1 or greater, and more preferably 10 or greater. Even more preferably, the mass ratio is in the range of 10 to 10,000. Alternately, the composition of the present invention can be prepared by combining apigenin with BHT, and adjusting the pH of the composition to a value less than 7. These procedures suppress the formation of an adduct of BHT and apigenin in the composition, and thus apigenin is stably maintained in the composition. According to a preferred embodiment, the apigenin retention ratio (the ratio of the amount of apigenin after storage for one month under the conditions of 50° C. with respect to the amount of apigenin after storage for the same time period at −5° C.) in the composition of the present invention is greater than 91%, more preferably 94% or greater, and even more preferably 96% or greater.

The pH of the composition of the present invention is not particularly limited and may be 7 or higher (for example, pH 7.0, pH 7.0 or higher, or higher than pH 7.0), or maybe lower than 7 (lower than pH 7.0) if the mass ratio of the content of apigenin relative to the content of BHT in the composition is kept adjusted to 1 or greater. Otherwise, the pH of the composition of the present invention is adjusted to less than 7. The pH of the composition of the present invention may be appropriately adjusted in the range described above, in accordance with the use of the composition or the like.

The pH value of the composition of the present invention is preferably less than 7, more preferably 6.8 or less, even more preferably 6.5 or less, and even more preferably in the range of pH 4 to 6.5. The pH of the composition can be adjusted by using a pH adjusting agent. There are no particular limitations on the pH adjusting agent as long as it is an agent generally used for the purpose, and examples include inorganic acids such as hydrochloric acid, sulfuric acid, nitric acid, carbonic acid, and phosphoric acid; organic acids such as citric acid, acetic acid, lactic acid, succinic acid, glycolic acid, ascorbic acid, malic acid, fumaric acid, tartaric acid, urea, ε-aminocaproic acid, and pyrrolidone carboxylic acid; betaines such as glycine betaine, and lysine betaine; inorganic alkalis such as metal hydroxides; organic amines such as guanidine, and 2-amino-2-methylpropane; alkanolamines such as ammonia, monoethanolamine, diethanolamine, triethanolamine, isopropanolamine, and diisopropanolamine; basic amino acids such as arginine, and lysine; and combinations thereof.

On the occasion of maintaining apigenin stably in the composition according to the present invention, there are no particular limitations on the contents (absolute amounts) of apigenin and BHT in the composition, and the contents may be appropriately adjusted in accordance with the dosage form and use of the composition and the like. For example, the content of apigenin may be 1 ppm by mass or greater, preferably 3 ppm by mass or greater, more preferably 5 to 50 ppm by mass, and even more preferably 7 to 25 ppm by mass, relative to the total mass of the composition. The content of BHT may be, for example, in the range of 0.001 to 500 ppm by mass, and preferably 0.01 to 10 ppm by mass, relative to the total mass of the composition. When an apigenin-containing extract is used in the preparation of the composition of the present invention, an appropriate amount of the extract is incorporated into the composition of the present invention so that the apigenin content in the final composition falls into the range described above.

In addition to apigenin, BHT and the pH adjusting agent described above, other active ingredients or optional additives can be added to the composition of the present invention in appropriate amounts according to the dosage form and use of the composition and the like. Examples of the additives include an excipient, a binder, a disintegrant, a lubricating agent, a diluent, an osmotic pressure adjusting agent, an emulsifier, an antiseptic agent, a stabilizer, an oxidation inhibitor, a colorant, an ultraviolet absorber, a moisturizer, a thickener, a gloss agent, an activity enhancer, an anti-inflammatory agent, an antibacterial agent, a fragrance, a flavoring agent and an odor masking agent. Examples of the other active ingredients include, in the case of a cosmetic composition, active ingredients other than apigenin, for example, other cosmetic and toiletry components such as a moisturizer, a skin lightening agent, an ultraviolet protective agent, a cell activator, a cleansing agent, a keratolytic agent and makeup components (e.g., cosmetic base, foundation, face powder, powder, blusher, lipstick, eye makeup, eyebrow makeup, mascara and others).

The composition of the present invention can be used as a medicine, a quasi-drug, a cosmetic material or the like, or as a raw material for these materials. The form of the composition is arbitrarily selected in accordance with the use of the composition. When the composition is used as a medicine or a quasi-drug, examples of the form of the composition include dosage forms for oral administration, such as a tablet, pill, capsule, liquid, syrup, powder and granule; dosage forms for parenteral administration, such as a solution, emulsion and suspension for injection, infusion, percutaneous, transmucosal, transnasal, enteric, inhalation, suppository and bolus preparations and the like; and dosage forms for topical administration, such as a cream, lotion, gel, sheet, patch and stick. Examples of the form in the case of using the composition for a cosmetic material include any forms that can be used in cosmetic materials, such as a cream, emulsion, lotion, suspension, gel, powder, mask pack, sheet, patch, stick and cake.

According to the present invention, since the formation of an adduct of BHT and apigenin that are contained in the composition is suppressed, apigenin in the composition is stably maintained. Therefore, according to the present invention, a composition which stably contains apigenin as an active ingredient and consequently exhibits the effect of apigenin to a maximum extent, is provided. In the composition provided by the present invention, apigenin is stably maintained, without the actions of apigenin (for example, a urease activity inhibitory action, an antioxidant action, a melanin production promoting action, an anti-inflammatory action, a pigmentation inhibitory action, or a skin lightening action) being deteriorated, and as a result, the composition exhibits excellent advantageous effects.

EXAMPLES

Hereinafter, the present invention will be described in more detail by way of Reference Examples and Examples, but the present invention is not intended to be limited to these Examples. In the following description, the unit ppm represents ppm by mass.

Example 1

Evaluation of Stability of Apigenin in Composition

Twenty gram of Roman chamomile was extracted with 200 mL of 50% butanediol for 7 days at room temperature, and then the extract was filtered to obtain 155 mL of a Roman chamomile extract. The evaporation residue in 1 mL of the extract was 18.6 mg, and the amount of apigenin in 1 mL of the extract was 305 ppm. This extract was used as the apigenin-containing extract in the following experiments.

Solutions having different pH conditions were prepared according to the formulations indicated in the following Table 1. BHT was added to each of the solutions of various pH conditions, in an amount of 0, 1, 10, 100 and 500 ppm, respectively, and thus test solutions (final apigenin concentration: about 9 ppm) were prepared. The respective test solutions were stored for one month under the conditions of −5° C. and 50° C., and then the amount of apigenin in each of the solutions was measured by HPLC (Inertsil ODS-3 (internal diameter 3.0 mm, length 150 mm, particle size 5 μm) manufactured by GL Sciences, Inc., eluent: 50% aqueous solution of 25 mM potassium dihydrogen phosphate/50% methanol, column temperature: 40° C., detection: UV 340 nm). The ratio of the amount of apigenin stored at 50° C. with respect to that stored at −5° C. was determined as the apigenin retention ratio.

TABLE 1

| | pH 6 | pH 6.5 | pH 7 | (mL)<br>pH 8 |
|---|---|---|---|---|
| 0.1 M Aqueous solution of $Na_2HPO_4$ | 9.80 | 11.48 | 12.78 | 15.09 |
| 0.1 M Aqueous solution of citric acid | 5.72 | 4.04 | 2.74 | 0.43 |
| EtOH | 15.52 | 15.52 | 15.52 | 15.52 |
| Roman chamomile extract (apigenin-containing extract) | 0.96 | 0.96 | 0.96 | 0.96 |
| Total | 32 | 32 | 32 | 32 |

The results are presented in the following Table 2. Under the conditions in which the mass ratio of the content of apigenin and the content of BHT was about less than 1 (BHT 10 ppm or more), and the pH value was 7 or higher, the apigenin retention ratio decreased, indicating that the formation of an adduct of apigenin and BHT had proceeded. On the other hand, when the mass ratio of the content of apigenin and the content of BHT was about 1 or greater, or when the pH value of the solution was less than 7, the formation of an adduct did not occur, and high retention ratios were maintained even after storage for a long time. That is, it was indicated that when the mass ratio of the content of apigenin and the content of BHT in the solution is adjusted to 1 or greater, or when the pH of the solution is adjusted to a value less than 7, apigenin is satisfactorily retained.

TABLE 2

| Apigenin retention ratio (amount of apigenin stored at 50° C./amount of apigenin stored at −5° C.) | | | | |
|---|---|---|---|---|
| | pH 6 | pH 6.5 | pH 7 | pH 8 |
| BHT 0 ppm | 103% | 100% | 96% | 98% |
| BHT 1 ppm | 102% | 94% | 96% | 99% |

TABLE 2-continued

| Apigenin retention ratio (amount of apigenin stored at 50° C./amount of apigenin stored at −5° C.) | | | | |
|---|---|---|---|---|
| | pH 6 | pH 6.5 | pH 7 | pH 8 |
| BHT 10 ppm | 98% | 98% | 98% | 91% |
| BHT 100 ppm | 96% | 96% | 82% | 73% |
| BHT 500 ppm | 96% | 99% | 35% | 11% |

In the test solutions where the apigenin retention ratio decreased, an adduct of apigenin and BHT represented by the following formula was formed.

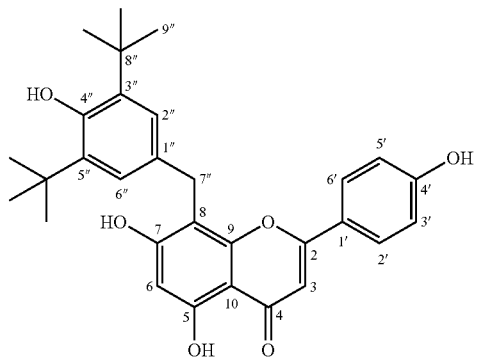 [SMILES: CC(C)(C)c1cc(Cc2c(O)cc(O)c3c(=O)cc(-c4ccc(O)cc4)oc23)cc(C(C)(C)C)c1O]

TABLE 3

Results of NMR analysis of adduct purified by HPLC
(Bruker AV600, solvent: DMSO-d6)

| | 1H | | | | 13C |
|---|---|---|---|---|---|
| | σ (ppm) | Integ | Peak | J (Hz) | σ (ppm) |
| 1 | | | | | |
| 2 | | | | | 165.5 |
| 3 | 6.69 | 1 | s | | 102.4 |
| 4 | | | | | 181.7 |
| 5 | | | | | 159.2 |
| 6 | 6.28 | 1 | s | | 98.8 |
| 7 | | | | | 163.4 |
| 8 | | | | | 107.2 |
| 9 | | | | | 154.5 |
| 10 | | | | | 102.8 |
| 1' | | | | | 121.2 |
| 2', 6' | 7.87 | 2 | d | 8.8 | 128.3 |
| 3', 5' | 6.89 | 2 | d | 8.8 | 116.0 |
| 4' | | | | | 161.5 |
| 1" | | | | | 132.1 |
| 2", 6" | 7.13 | 2 | s | | 124.4 |
| 3", 5" | | | | | 139.0 |
| 4" | | | | | 151.7 |
| 7" | 3.94 | 2 | s | | 27.9 |
| 8" | | | | | 34.4 |
| 9" | 1.24 | 18 | s | | 30.3 |

Reference Example

Skin Lightening Effect of Apigenin (Preparation of Test Sample)

By using the Roman chamomile extract prepared in Example 1, test samples having the compositions indicated in Table 4 were prepared to evaluate the skin lightening effect of apigenin.

TABLE 4

| | Test sample | | Comparative sample (placebo) |
|---|---|---|---|
| Component (mass %) | 1 | 2 | 1 |
| Roman chamomile extract | 5 | 1 | 0 |
| (apigenin concentration ppm) | (15) | (3) | (—) |
| Ethanol | 50 | 50 | 50 |
| 1,3-Butylene Glycol | 25 | 25 | 25 |
| Ion-exchanged water | Balance | Balance | Balance |

(Evaluation of Skin Lightening Effect)

The color of the skin at the inner part of the upper arm of ten normal male and female subjects was measured using a color difference meter (CMS-35FS manufactured by Murakami Color Research Laboratory Co., Ltd.), and the initial L* values were calculated from the Munsell values thus obtained. The skin at the site where the skin color was measured, was irradiated once with ultraviolet radiation in the UV-B region at a dose equivalent to 2 times the minimum erythematous dose (2 MED), using an FS-20SE lamp manufactured by Toshiba Corporation. Thereafter, each of the samples (Test samples 1 and 2, and Comparative sample 1) was continuously applied on the same site two times a day for 3 weeks. The skin color measurement using a color difference meter was carried out again, and the L* values were calculated from the Munsell values thus obtained. The amount of change (ΔL*) in the L* value of the skin at the sample-applied site relative to the initial value was calculated for each of the Test samples 1 and 2 and Comparative sample 1. The average value (n=10) of the ΔL* value was calculated for each of the samples. A paired t-test was carried out using the average value of the ΔL* value of the skin at the Test sample 1-applied site or the Test sample 2-applied site, and the average value of the ΔL* value of the skin at the Comparative sample 1-applied site, and thereby the significance level (p value) was determined as an index for the evaluation of the skin lightening effect. The results are presented in Table 5.

TABLE 5

| | Test sample | | Comparative sample (placebo) |
|---|---|---|---|
| | 1 | 2 | 1 |
| Average value of ΔL* value after 3 weeks | 3.491 | 3.54 | 3.752 |
| t-test significance level with Comparative Example | p = 0.0178 | p = 0.0954 | |

From the results of Table 2, the sample incorporated with a 5 mass % Roman chamomile extract (containing 15 ppm of apigenin) was proved to have a significant effect of suppressing the ΔL* value as compared with the comparative sample (placebo), and thus the sample was recognized to have an excellent skin lightening effect. Also in the case of the sample incorporated with a 1 mass % Roman chamomile extract (containing 3 ppm of apigenin), the sample was proved to have a tendency of suppressing the ΔL* value as compared with the comparative sample (placebo), and thus it was suggested that the sample has a skin lightening effect.

Preparation Example

Skin Lightening Composition

A skin toner at pH 6 having the following composition was prepared.

| (Composition) | (Content: mass %) |
|---|---|
| Roman chamomile extract | 5 |
| Ethanol | 20 |
| 1,3-Butylene glycol | 25 |
| BHT | 0.001 |
| Purified water | Balance |

What is claimed is:

1. A method for preparing an apigenin-containing composition, the method comprising combining 3 ppm or more of apigenin by mass with dibutylhydroxytoluene, and adjusting the mass ratio of the content of apigenin relative to the content of dibutylhydroxytoluene to be 1 or greater.

2. The method according to claim 1, wherein the composition is a skin lightening composition.

3. The method according to claim 2, wherein the pH value of the composition is or is adjusted to be 6.8 or less.

4. The method according to claim 3, wherein the pH value of the composition is or is adjusted to be 6.5 or less.

5. The method according to claim 2, wherein the apigenin retention ratio in the composition after storage for one month under the conditions of 50° C. is greater than 91%.

6. The method according to claim 1, wherein the pH value of the composition is or is adjusted to be 6.8 or less.

7. The method according to claim 6, wherein the pH value of the composition is or is adjusted to be 6.5 or less.

8. The method according to claim 1, wherein the apigenin retention ratio in the composition after storage for one month under the conditions of 50° C. is greater than 91%.

9. A method for stabilizing apigenin in a composition containing apigenin and dibutylhydroxytoluene, the method comprising adjusting the mass ratio of the content of apigenin relative to the content of dibutylhydroxytoluene to be 1 or greater.

10. The method according to claim 9, wherein the pH value of the composition is or is adjusted to be 6.8 or less.

11. The method according to claim 10, wherein the pH value of the composition is or is adjusted to be 6.5 or less.

12. The method according to claim 9, wherein the apigenin retention ratio in the composition after storage for one month under the conditions of 50° C. is greater than 91%.

13. A method for preparing an apigenin-containing composition, the method comprising combining 3 ppm or more of apigenin by mass with dibutylhydroxytoluene, and adjusting the pH of the composition to a value less than 7.

14. The method of claim 13, wherein the mass ratio of apigenin relative to dibutylhydroxytoluene is less than one.

15. The method according to claim 14, wherein the apigenin retention ratio in the composition after storage for one month under the conditions of 50° C. is greater than 91%.

16. The method according to claim 13, wherein the composition is a skin lightening composition.

17. The method according to claim 13, wherein the pH value of the composition is or is adjusted to be 6.8 or less.

18. The method according to claim 17, wherein the pH value is or is adjusted to be 6.5 or less.

19. The method according to claim 13, wherein the apigenin retention ratio in the composition after storage for one month under the conditions of 50° C. is greater than 91%.

20. A method for stabilizing apigenin in a composition containing apigenin and dibutylhydroxytoluene, the method comprising adjusting the pH of the composition to a value less than 7.

21. The method of claim 20, wherein the mass ratio of apigenin relative to dibutylhydroxytoluene is less than one.

22. The method according to claim 21, wherein the apigenin retention ratio in the composition after storage for one month under the conditions of 50° C. is greater than 91%.

23. The method according to claim 20, wherein the composition is a skin lightening composition.

24. The method according to claim 20, wherein the pH value of the composition is or is adjusted to be 6.8 or less.

25. The method according to claim 24, wherein the pH value is or is adjusted to be 6.5 or less.

26. The method according to claim 20, wherein the apigenin retention ratio in the composition after storage for one month under the conditions of 50° C. is greater than 91%.

* * * * *